United States Patent
Oresic et al.

(10) Patent No.: US 8,572,064 B2
(45) Date of Patent: Oct. 29, 2013

(54) VISUALIZATION TECHNIQUE FOR BIOLOGICAL INFORMATION

(75) Inventors: Matej Oresic, Espoo (FI); Erno Lindfors, Helsinki (FI); Gopalacharyulu Peddinti, Helsinki (FI)

(73) Assignee: Valtion Teknillinen Tutkimuskeskus, Espoo (FI)

( * ) Notice: Subject to any disclaimer, the term of this patent is extended or adjusted under 35 U.S.C. 154(b) by 1374 days.

(21) Appl. No.: 11/912,900

(22) PCT Filed: Apr. 26, 2006

(86) PCT No.: PCT/FI2006/050163
§ 371 (c)(1),
(2), (4) Date: Jan. 12, 2008

(87) PCT Pub. No.: WO2006/114479
PCT Pub. Date: Nov. 2, 2006

(65) Prior Publication Data
US 2008/0162541 A1    Jul. 3, 2008

(30) Foreign Application Priority Data
Apr. 28, 2005 (FI) ....................... 20055198

(51) Int. Cl.
*G06F 19/00* (2011.01)
*G06F 17/00* (2006.01)

(52) U.S. Cl.
USPC ...................................... 707/707; 707/796

(58) Field of Classification Search
USPC .................. 707/E17.005, E17.008, E17.032, 707/999.102, 707–712, 722, 724, 793–796, 707/797, 798
See application file for complete search history.

(56) References Cited

U.S. PATENT DOCUMENTS

| | | | |
|---|---|---|---|
| 6,741,983 B1 * | 5/2004 | Birdwell et al. | 1/1 |
| 6,873,914 B2 * | 3/2005 | Winfield et al. | 702/19 |
| 2004/0153430 A1 * | 8/2004 | Sayad | 706/61 |

FOREIGN PATENT DOCUMENTS

| | | |
|---|---|---|
| EP | 1318472 A2 | 6/2003 |
| WO | WO 02/11048 | 2/2002 |
| WO | WO 02/103608 | 12/2002 |
| WO | WO 03/067504 | 8/2003 |
| WO | WO 03/081468 | 10/2003 |

OTHER PUBLICATIONS

Gopalacharyulu et al, Data integration and visualization system for enabling conceptual biology, pp. 177-185, Mar. 27, 2005, Line Numbers Added to reference.*
Baruchi, I. et al. "Functional holography of complex networks activity—From cultures to the human brain" Complexity, vol. 10, No. 3, Jan. 2005, pp. 38-51.
Nilsson, J. et al. "Approximate geodesic distances reveal biologically relevant structures in microarray data" Bioinformatics (Oxford), vol. 20, No. 6, Apr. 12, 2004, pp. 874-880.

* cited by examiner

*Primary Examiner* — Jacob F Bétit
*Assistant Examiner* — Amanda Willis
(74) *Attorney, Agent, or Firm* — Young & Thompson (57) ABSTRACT

Method/system for visualizing biological information. The system receives a user query relating to biological information and determines which database contains related biological information. A database query is sent to the database and the result indicates biological/chemical entities and relations. A network is created based on the result; biological/chemical entities are mapped to network nodes and relations to network connections. A distance matrix indicates a multi-dimensional distance for several pairs of network nodes. A dimensionality reduction function is adjusted based on a research context, to bias the search toward a relevant focus. The number of dimensions in the distance matrix is lowered by the dimensionality reduction function. Neighbors of a selected node are searched (2-18) based on the distance matrix to elucidate a biological role of the selected node. A re-created network is visualized (2-20) based on the adjusted dimensionality reduction function.

13 Claims, 8 Drawing Sheets

410A — `<?xml version="1.0" encoding="utf-8"?>`
`<protein created="1988-04-01" dataset="Swiss-Prot" ino:id="3426" updated="2004-07-05">`
  `<primaryid>P07242</primaryid>`
  `<entry>AG35_VACCV</entry>`
  `<name>Envelope protein</name>`
  `<synonym>Protein H5</synonym>`
  `<synonym>Protein H6</synonym>`

420
  `<organism>`
    `<name>Vaccinia virus (strain WR)</name>`
    `<dbref id="10254" type="NCBI Taxonomy"/>`
  `</organism>`

430
  `<gene>`
    `<name>AG35</name>`
    `<synonym>H5R</synonym>`
    `<dbref id="M13209" type="EMBL">`
      `<property type="protein sequence ID" value="AAB59841.1"/>`
    `</dbref>`
    `<dbref id="M23648" type="EMBL">`
      `<property type="protein sequence ID" value="AAA47962.1"/>`
    `</dbref>`
  `</gene>`

440A — `<dblinks>`
442
  `<dbref id="F24481" type="PIR">`
    `<property type="entry name" value="QQVZH6"/>`
  `</dbref>`

`<dbref id="IPR004966" type="InterPro">`
    `<property type="entry name" value="Pox_Ag35"/>`
  `</dbref>`

`<dbref id="PF03286" type="Pfam">`
    `<property type="entry name" value="Pox_Ag35"/>`
  `</dbref>`

`<dbref id="138380" type="GenInfo"/>`

440B — `</dblinks>`
410B — `</protein>`

Glycolysis / Gluconeogenesis AND Pentose phosphate pathway AND TCA cycle IN S. cerevisiae

Fig. 7B

VISUALIZATION TECHNIQUE FOR BIOLOGICAL INFORMATION

BACKGROUND OF THE INVENTION

The invention relates to visualization techniques for visualizing biological information. It is customary to organize biological relations as one or more pathways or networks. An exemplary system is disclosed in Hass, L et al: *"Discovery-Link, a system for integrated access to life science data sources"*, IBM Systems Journal 40, p. 489-511. The system described in this article exhibits certain shortcomings, however.

Historically, the decomposition of biology into different disciplines was necessary to tackle the complexity of life science systems by reducing the degree of complexity down to the most basic level. With the advent of systems biology, such separation of biology is increasingly becoming artificial. But the long history of separating biology to different disciplines hampers attempts to integrate biological information. For instance, different databases often use mutually incompatible naming conventions and vocabularies. Attempts to solve such problems have been based on ontologies and semantic web technologies, such as XML (eXtendible Markup Language) and RDF (Resource Description Framework).

The ontology-based technologies attack the incompatibility problem at a relatively low level and only solves problems caused by the different naming conventions and vocabularies. The ontology-based technologies are unable to solve problems relating to problems caused by different context, ie, entities that may appear closely related in one context may be further apart in another. Another problem of known visualization systems is that they require extensive knowledge of the various software tools and databases.

BRIEF DESCRIPTION OF THE INVENTION

An object of the present invention is to provide a method and an apparatus for implementing the method so as to alleviate the above disadvantages. The object of the invention is achieved by the methods and equipment which are characterized by what is stated in the independent claims. The preferred embodiments of the invention are disclosed in the dependent claims.

An aspect of the invention is a method according to claim 1. Another aspect of the invention is a computer program product which comprises program routines for executing the method when the computer program product is executed in a computer system. Yet another aspect of the invention is a computer system which comprises such a computer program product.

The invention is, at least partially, based on the idea of extending the concept of "network" such that a large variety of biological entities can be mapped to network nodes and interrelations between the entities can be mapped to inter-node connections.

The invention is also based on a smart and integrated database query engine that is able to determine which of several databases contains the biological information relevant to a user's query. The result of the database query, or results from several queries, is/are mapped to an information network such that the biological entities are mapped to network nodes and the relations to network connections.

The invention is further based on a determining a distance matrix for indicating a distance between several pairs of network nodes, wherein each distance is measured across several dimensions. For instance, the distance matrix can be implemented as a data structure with two input values. The output of the data structure is a multi-dimensional distance between two entities that correspond to the two input values. The several dimension can be mapped to physical coordinates or similarity or correlation quantities or to any combination of such variables.

A distance function is then applied to map the multidimensional distance matrix to a smaller number of dimensions. For example, a three-dimensional distance matrix can be mapped to a two-dimensional one. Neighbours of a selected network node are searched based on the mapped distance matrix.

The distance function is adjusted depending on context. For example, a distance function optimized for diabetes research may not be optimal for cancer research, because even the same proteins may be involved in different mechanisms and pathways related to the two diseases, which is why the function of the protein can context-dependent. The network is then re-created and visualized based on the adjusted distance function.

An advantage of the smart database retrieval engine is that the user needs to specify only what kind of information he/she is interested in, without having to specify what database the information is located in.

An advantage of the adjustable distance function is that elements that are strongly interrelated in the user's current context are also topologically close to each other in the visualized network.

In an embodiment of the invention, the distance function is based on network topology, ie, a measure of connectivity. For instance, the distance function between two entities may be a three-dimensional vector representation of a shortest path between the two entities.

Instead of network topology, or in addition to it, the distance function may be based on relationships derived from experimental data. An advantage of this feature is that the similarities derived from experimental data can complement the existing knowledge, and through that provide a framework for generating new knowledge on complex biological processes.

In an embodiment of the invention, the user interface provides the user with means for determining the distance(s) as part of the database query. This is beneficial since the distance basically determines the context of the questions posed by the user. Is further allows biasing the similarity toward particular types of relationships, or towards a relationship in a specific context. Once the distance measure is specified, the system can map the network nodes into a lower-dimensional space. Because the mapping is approximate, it will introduce some distortion. Therefore the exact form of the mapping is not critical as long as it emphasizes relationships in the context graph. It is ultimately the end result of the data mining that determines the utility of a specific distance measure, and the user is preferably provided with an option to experiment with several different distance measures.

Sammon's mapping is a good mapping scheme for network visualization. It maps the network graph nonlinearly into a lower-dimensional space while preserving the inter-node distances across the network. It is not a perfect choice for interactive addition of new nodes, however, because the mapping of the entire (sub)network must be recomputed each time a new node is added. For interactive network construction or editing, multidimensional scaling methods (see Torgerson 1952, a list of references is at the end of this description) or self-organizing maps (Kohonen 2001) can be used. The non-metric multidimensional scaling method disclosed by Cox and Cox is focused on preserving the order of similarities, and appears to be promising mapping scheme in connection with the present invention.

BRIEF DESCRIPTION OF THE DRAWINGS

In the following the invention will be described in greater detail by means of preferred embodiments with reference to the attached drawings, in which.

DETAILED DESCRIPTION OF EMBODIMENTS OF THE INVENTION

Figure 1:
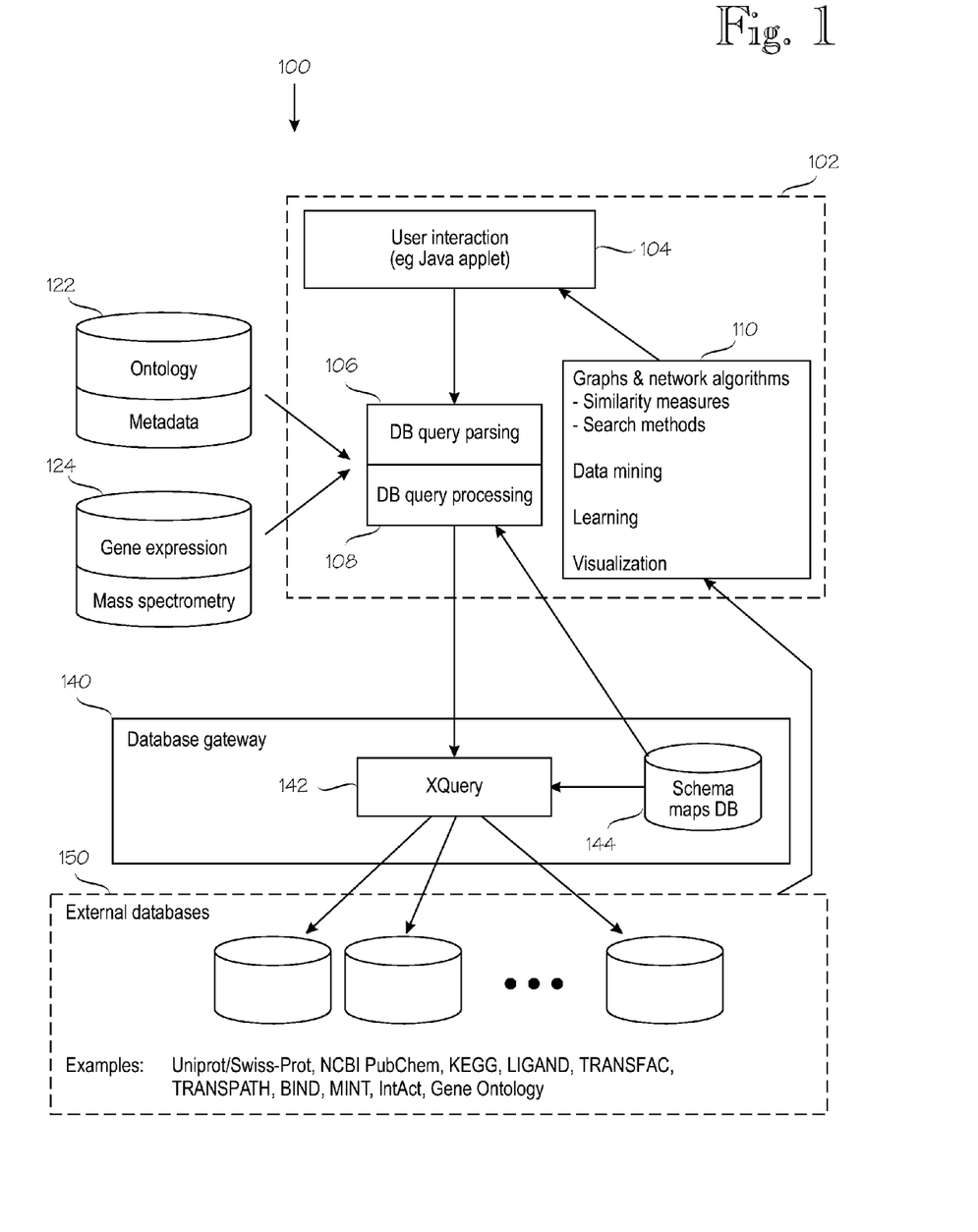
FIG. 1 shows an overall view of an exemplary system architecture.

FIG. 1 shows an overall view of a system architecture 100 according to an illustrative but non-restricting embodiment of the invention. The main structural sections of the system 100 are a network processing block 102, local databases 122 and 124, a database gateway 140 and a set of external databases 150. As regards data integration and visualization, the system comprises three layers. The data in the external databases 150 constitute a back-end layer, the user interface 104 in the network processing block 102 constitutes a front-end layer, while everything else occupies the middle layer, including the database gateway 140, which in turn includes an XQuery processing block 142 and a schema mapping database 144, as well as ontology definitions and metadata 122, graph and network algorithms 110, learning mechanisms, etc.

In this embodiment, a first local database 122 stores ontology data and metadata in XML language, which is easily parsed by computers. A suitable Linux server system for storing such data is sold under the name of Tamino by Software AG. The external databases are queried using Tamino XQuery, which is an implementation of XQuery language. In one implementation, the queries are passed via a Java API (application programming interface) in the Tamino server. A second local database 124 stores more voluminous data, such as gene expression data or mass spectrometry data. The second local database 124 can be implemented by Oracle® technology and queried via Java Database Connectivity (JDBC), for example.

The query parsing and processing blocks 106, 108, support parallel data retrieval across multiple external databases. The graph and network analysis block 110 processes the results of the database queries and present the results as a network or multiple subnetworks. The nodes of the network represent biological or chemical entities, such as proteins, genes, compounds, DNA binding sites, or the like. Inter-node connections have associated attributes which contain information about one or more of the following: types of relationships, quantitative of semantic information (such as "is located in" in case of a linking a protein with a complex entity such as a cell organelle). The query parsing and processing blocks 106, 108 retrieve biological data from the first local database 122 via a Java API interface and from the second local database 124 via JDBC.

The user interface UI in the network processing block NP interacts with the user. The user interface receives input from a user, such as navigation and data query instructions. The user input is processed and the processed result is provided as a visualized representation of the biological network. In an illustrative embodiment, the user interface block UI is implemented using Java Swing libraries. The network visualization can be implemented by means of visualization toolkits, such as Tom Sawyer Visualization Toolkit by Tom Sawyer, Inc.

Figure 2:
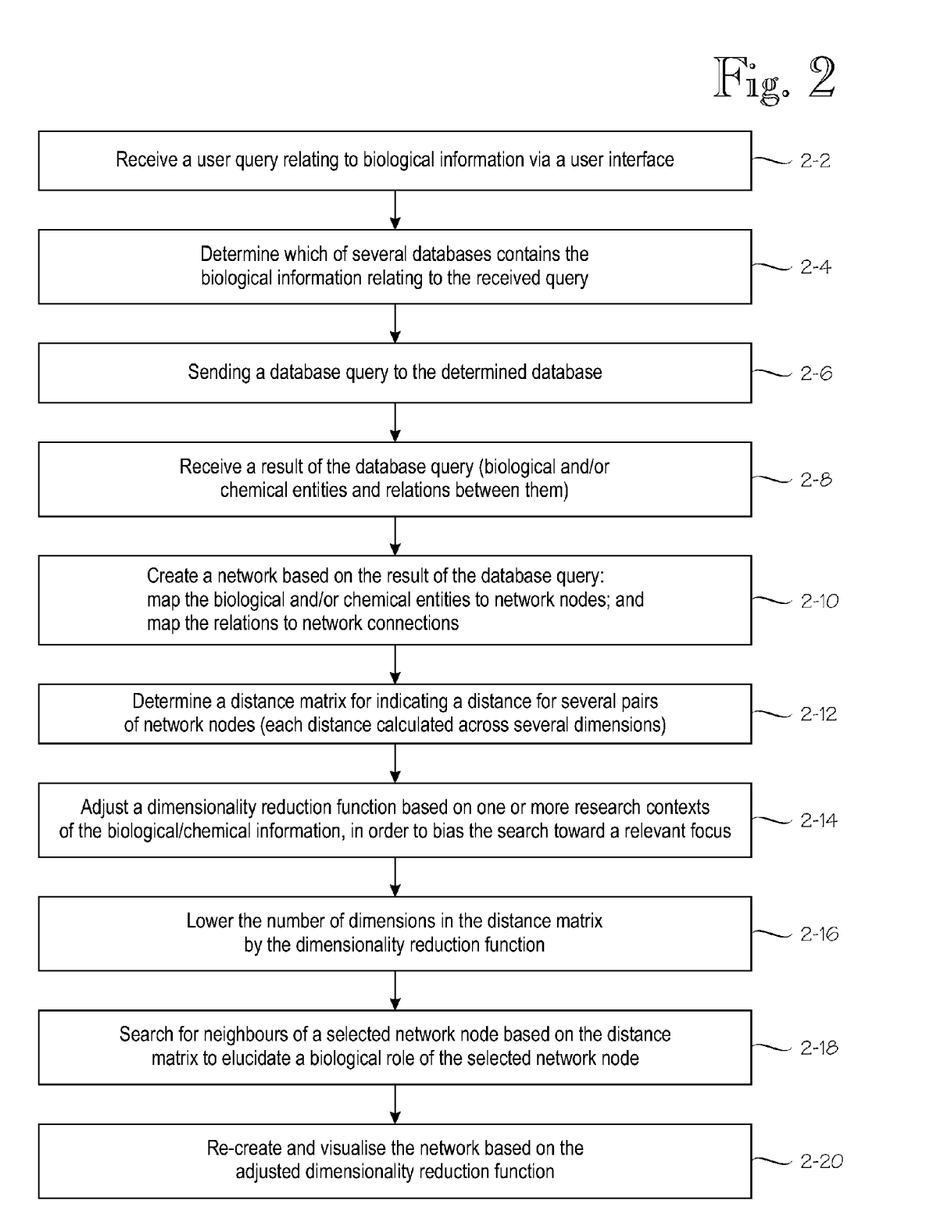
FIG. 2 shows an overall view of a method according to an embodiment of the invention.

FIG. 2 shows an overall view of a method according to an embodiment of the invention. In step 2-2 the system receives a user query relating to biological information via a user interface. In step 2-4, the system determines which of several databases contains the biological information relating to the received query. In step 2-6, the system sends a database query to the determined database. In step 2-8, the system receives a result of the database query (biological and/or chemical entities and relations between them). Next, in step 2-10, the system creates a network based on the result of the database query: the network creation comprises mapping the biological and/or chemical entities to network nodes and mapping the relations to network connections. In step 2-12, the system determines a distance matrix for indicating a distance for several pairs of network nodes (each distance calculated across several dimensions). In step 2-14, the dimensionality reduction function is adjusted based on one or more research contexts of the biological and/or chemical information, in order to bias the search toward a relevant focus. Step 2-16 comprises lowering the number of dimensions in the distance matrix by the dimensionality reduction function. In step 2-18, the system searches for neighbours of a selected network node based on the distance matrix to elucidate a biological role of the selected network node. In step 2-20 the network is re-created and visualised based on the adjusted dimensionality reduction function.

Figure 3:
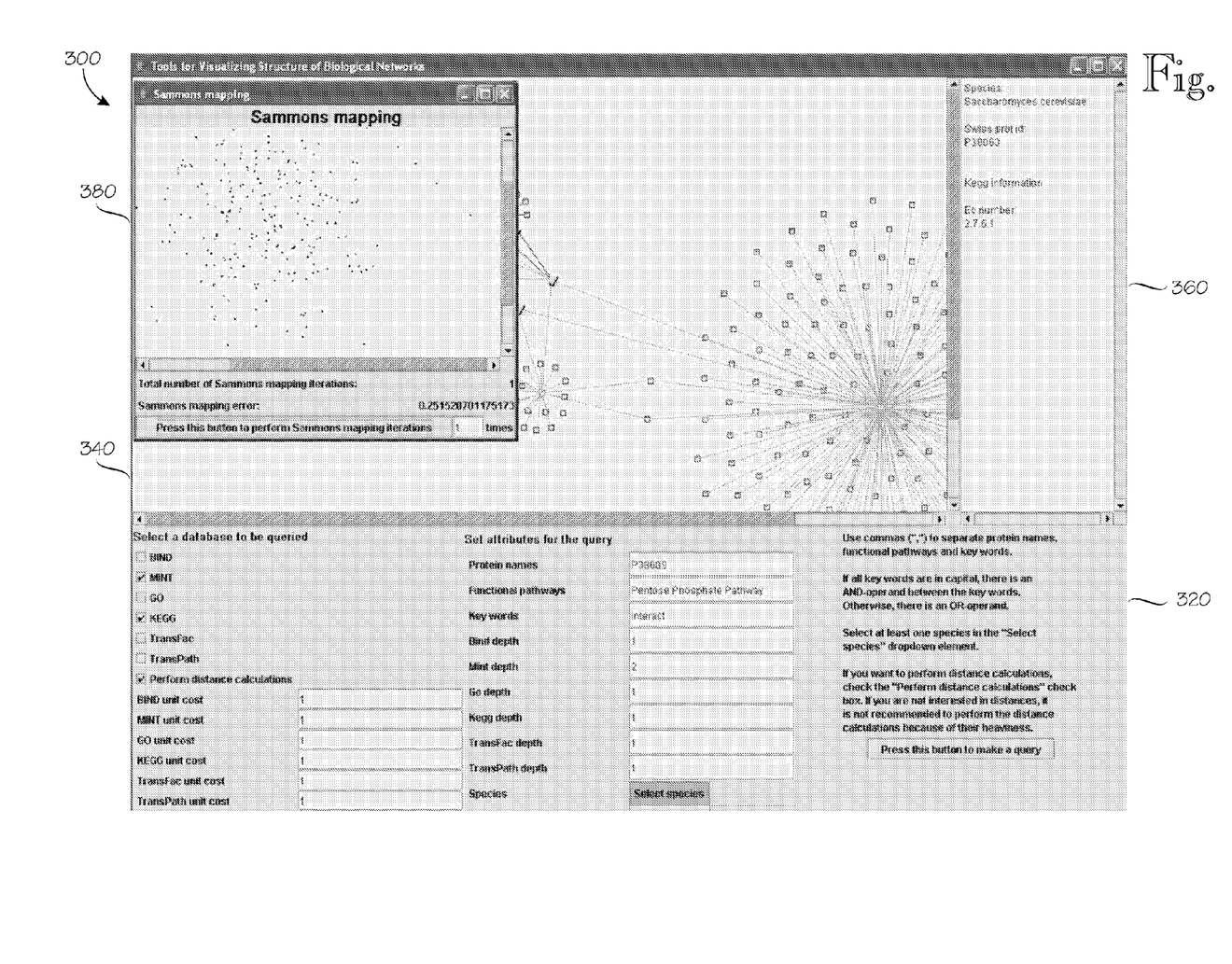
FIG. 3 shows a view generated by a user interface according to an embodiment of the invention.

It should be noted, however, that some or all of the above steps are typically repeated in an iterative process, and the order of the steps may be varied to some degree, while the results of a previous iteration are applied to the next iteration.
Database Integration FIG. 3 shows a screen 300 generated by the user interface according to an embodiment of the invention. In this example, the user interface screen 300 comprises a query section 320, a network display section 340, a text area section 360 and a distance mapping section 380. In this embodiment, the purpose and interrelation of these sections is as follows. The user defines a suitable query in the query section 320. The resulting biological network, or a sub-network of it, is visualized and displayed in the network display section 340. Whenever the user selects an entity displayed in the network display section 340, eg, by performing a mouse click on a node or connection, relevant information on the user-selected entity is displayed in the text area section 360. The information on the selected entity is retrieved from the local databases LD1, LD2, as well as from the external databases ED.

In one implementation, the user interface comprises a logic that takes as input a user-select node or a set of nodes, and permits the user to change options, such as a new search depth for the neighbours of the node(s). In the resultant subnetwork, shape conventions are used to distinguish the type of entity underlying the node(s). Colour codes can be used to distinguish the type of the relationship underlying the connections. The resultant subnetwork can be extracted and exported in XML format.

Data from various biological and chemical databases 150 is collected into the local database system. By way of example, the embodiment described herein can be used at least in connection with the following databases:
  Uniprot/Swiss-Prot
  NCBI PubChem
  KEGG
  LIGAND
  TRANSFAC
  TRANSPATH
  BIND
  MINT
  DIP
  Intact
  Gene Ontology In order to couple an external database into the system 100, certain preparatory acts must be performed. These acts can be described in the form of an algorithm as follows.
  (i) Decide on a data source to be set up; download the data (typically by using FTP). If the downloaded data is in XML format, go to step (iii), otherwise continue at step (ii).
  (ii) Study the structure of the non-XML data and define XML schemas to capture the logical structure of the data; go to step (iv).
  (iii) If the document structures have been defined using DTD, then convert the DTD to W3C Schema; if the XML Schema is available from the source itself, then if necessary, make changes to it to fit the implementation requirements (eg change the target namespace to the namespace of local database 122 (eg Tamino™) and define a prefix for the original target namespace).
  (iv) Define physical properties, such as indices, doctype, etc., for the logical schema to construct a schema definition document compatible with the local database 122 (eg in case of a Tamino™ database, a Tamino Schema Definition document, TSD would be constructed); if the previous step was (ii), go to step (v), else to step (vi).
  (v) Develop parsers to convert the non-XML data into an XML format. A typical development phase is always followed by several test-and-feedback loops that involve an extensive use of XML data validation as well as reading by humans. Go to step (vii).
  (vi) Develop parsers to convert the distributed XML format to the required XML format.
  (vii) Load the resulting XML documents using mass-loading tools of the local database 122 (eg Tamino™ server).

In the course of implementing the above steps, the inventors have used XMLSPY software (Altova, Inc.) and Tamino™ Schema Editor software (Software AG) for the construction and validation of logical and physical schemas, respectively. The required parsers can be implemented in Perl or Java programming languages.

Figure 4:
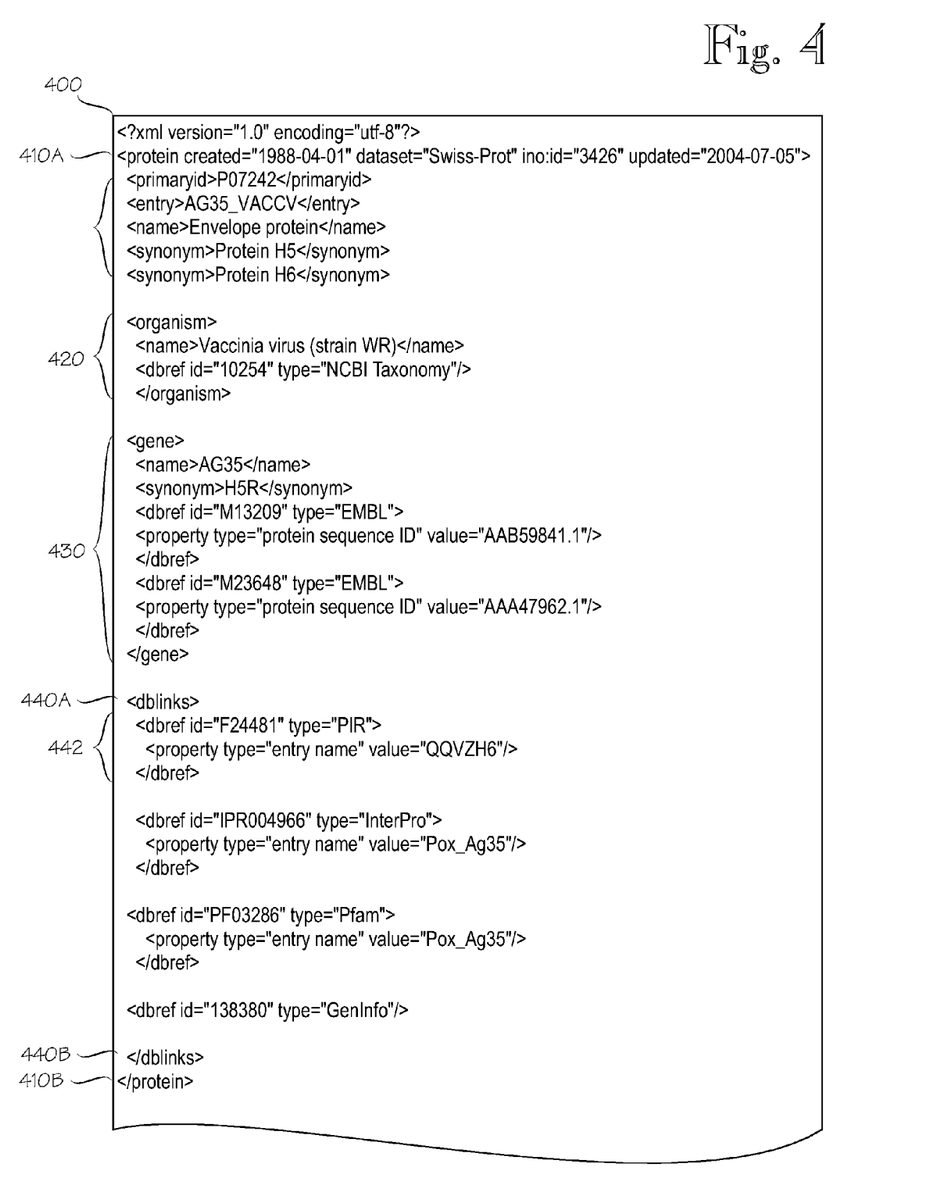
FIG. 4 shows an XML file for mapping across different names used similar entities in different databases.

FIG. 4 shows an XML document 400 for mapping across different names used similar entities in different databases. In this example, the XML document 400 performs a mapping from maps database for Uniprot protein entry AG35_VACCV, with links to indices from databases such as EMBL, PIR, INTERPRO and Pfam. In the XML document 400, indentations and empty lines are for the convenience of a human reader, computers ignore them. Lines 410A and 410B delineate a definition of a protein in a certain external database. In addition to beginning a definition block for the protein, line 410 contains a dataset name (here: "Swiss Prot") and an identifier (here: "3426"). Section 420 defines an organism in which the protein data is valid. Section 430 defines a gene which encodes the protein. Lines 440A and 440B delineate a section for database links. For example, section 442 provides a link to "PIR" database.

In the embodiment described here, database traversals are achieved by applying simple join operations involving the schema maps database 144. The fact that the schema maps database records contain identifiers and names of one or more entities from all databases ensures that a join operation between appropriate databases and rightly chosen entities will always return a non-empty result. The querying of a database independent of the names used in it can be achieved by writing two-phase queries to first search the schema maps database 144 to find out the name/ID number of the entity in the original database and then search the original database with the correct name/ID number.

Another problem is caused by often-changing data structures in public databanks. In a further preferred embodiment of the invention, this problem is solved by keeping the logical schemas as minimal as possible, yet useful enough to support observation of associations between all the data sources.

Figure 5A:
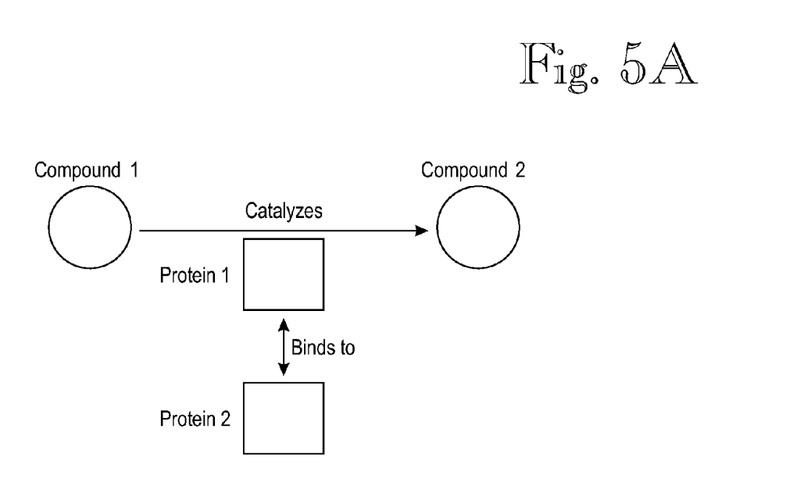
FIG. 5A shows a schematic representation of relationships between two compounds and two proteins.
Figure 5B:
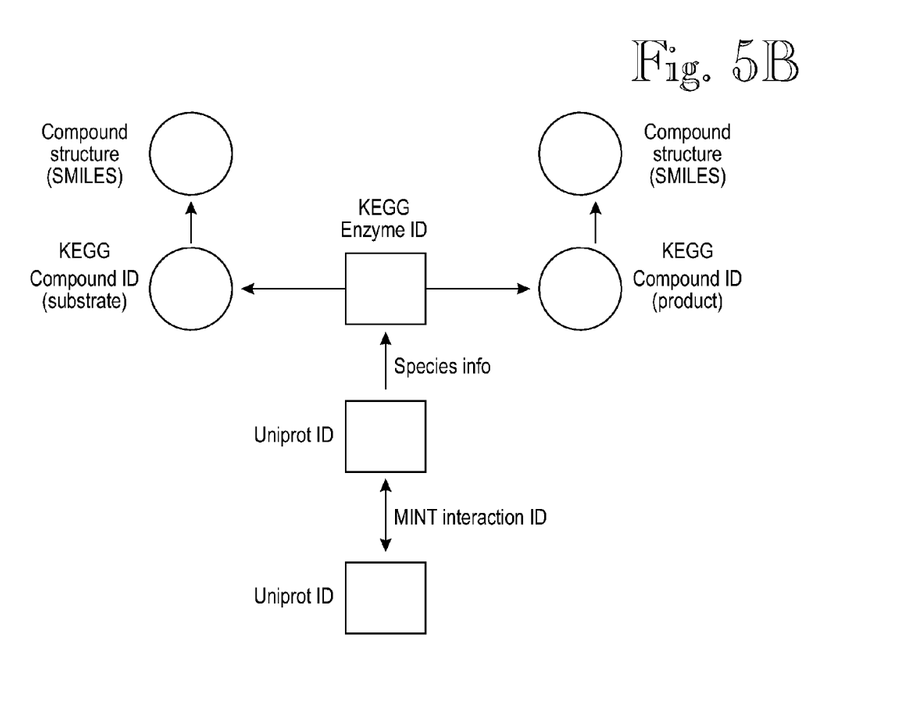
FIG. 5B shows the representation shown in FIG. 5A as hypothetically resolved via traversals across multiple databases.

FIG. 5A shows a schematic representation of relationships between two compounds and two proteins. FIG. 5B shows the representation shown in FIG. 5A as hypothetically resolved via traversals across multiple databases. For instance, database traversals can be resolved using the XML schema maps as described above and in connection with FIG. 4, so that the user does not need to know about the background of the traversals. Instead, the user interacts with the system only at the level of biological entities as shown in FIG. 5A.

Figure 6:
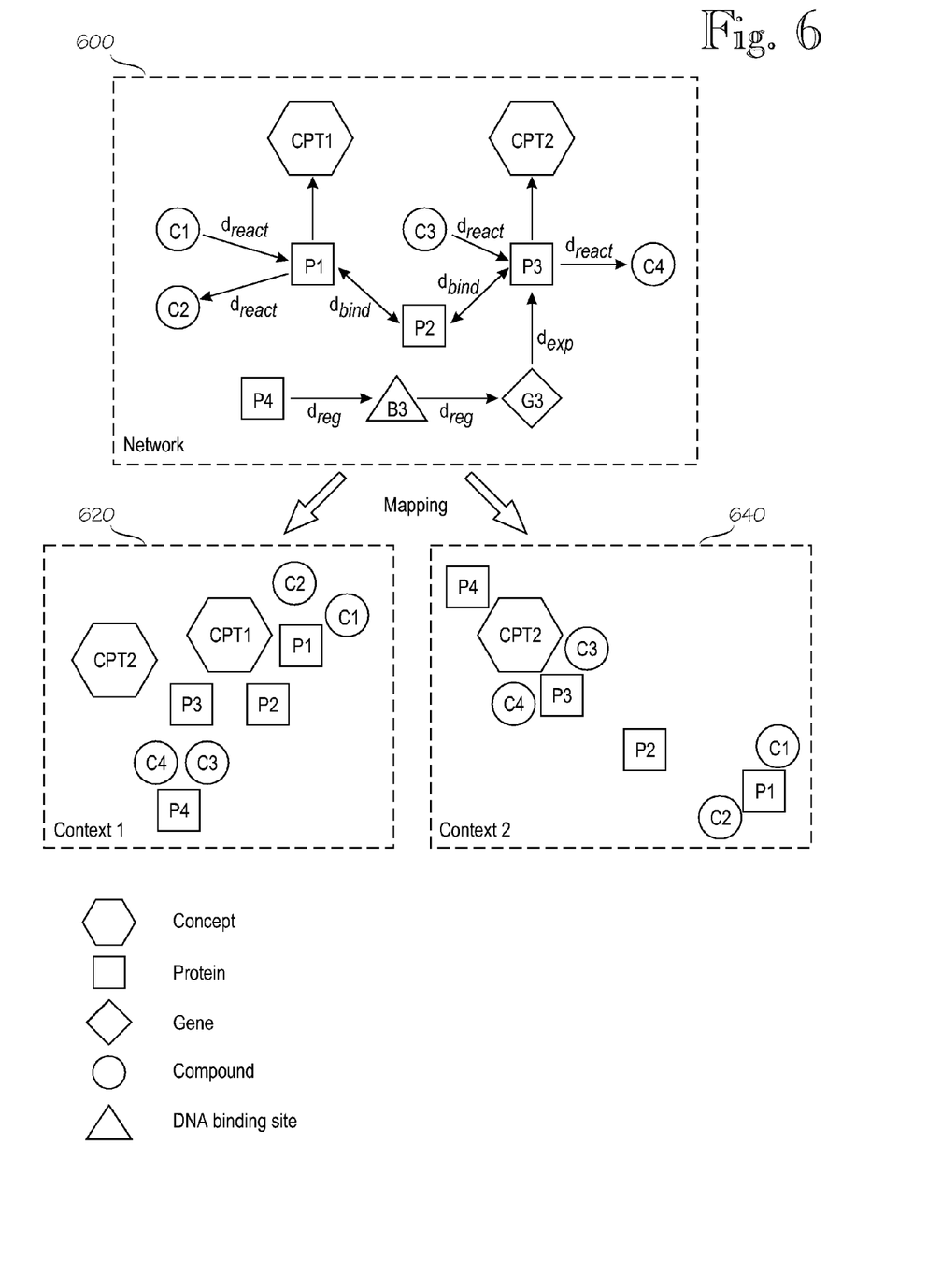
FIG. 6 shows a biochemical network with two different concept nodes and two different mappings for two different contexts.

FIG. 6 shows a hypothetical biochemical network 600 with two different concept nodes CPT1 and CPT2. Reference numerals 620 and 640 denote two different mappings of the network 600, wherein mappings result from different weightings. In one illustrative implementation, the mapping can be accomplished by means of some clustering mechanism, such as a self-organizing map (SOM). Reference numeral 620 denotes a mapping after a context-neutral weighting of relationships (concepts CPT1 and CPT2 are weighted equally), while numeral 640 denotes a mapping after a weighting of relationships which emphasizes concept CPT2. In the mappings 620 and 640, only the protein and compound nodes in distance calculations were considered, while inter-node connections are omitted for clarity.

For instance, a concept can be the name of biological process or information on localization within a cell or specific tissue. The context, in turn, describes the user's domain of relevance as expressed in query, such as "is related to diabetes" or "is localized within the adipose tissue".

Similarity Measures and Graph Projection

Property of similarity plays an important role in any perception and formation of new concepts. To this end, the network visualization tool should be able to evaluate similarity (or its inverse quantity, distance) between any two entities. It should be understood that distance (as a measure of similarity) is not a straightforward geometrical two- or three-dimensional quantity but involves a large number of dimensions. By way of example, such dimensions can mean relationships of different types, ie, chemical reactions, protein-protein interactions, gene sequence comparisons or more complex relationships like protein localization, gene-phenotype association or compound properties. The task of evaluating similarity or distance becomes more complex with increasing number of dimensions.

While distances within the molecular networks can be intuitively set to the length of the shortest path between the molecules, distance measure is less obvious for relationships such as in ontologies. A gene ontology can be represented as a graph or tree. In the case of an ontology tree, for example, we can assign a distance based on the closest common ancestor in the graph. When combining multiple relationships and corresponding distance measures, reasonable normalization of distance values has to be set in order to be able to compare across heterogeneous data sources. The distances between entities that do not have a direct relationship are then calculated as the lengths of the shortest paths with the distance-weighted connection, as explained in the description of FIG. 6.

After distance normalization, an importance factor and, hence, distance bias can be assigned to any particular relationship type, whereby context sensitivity can be achieved, as described in connection with FIG. 6. When visualizing such complex data, it is often beneficial to lower the number of dimensions, ie, to project the complex data into a space with fewer dimensions. In doing so it is important to preserve distances. This means that any two samples that are close to each other in the original space should stay close to each other when projected. Conversely, two entities that are close to each other in the projected space must have come from samples that were close to each other in the original space. This type of mapping is referred to as Sammon's mapping, which is implemented in a preferred embodiment of the network visualization routine 110 (FIG. 1).

Visual configuration of entities can be estimated with a gradient descent type of algorithm on a cost function based on the inter-point distances between the entities in the original space and the introduced discrepancies when applying the dimensionality-reducing mapping. In this way, the visual configuration approximates the original relationships in the complex networks. This kind of distance preservation is also used in self-organizing maps (SOM) invented by Teuvo Kohonen.

EXAMPLES

Figure 7A:
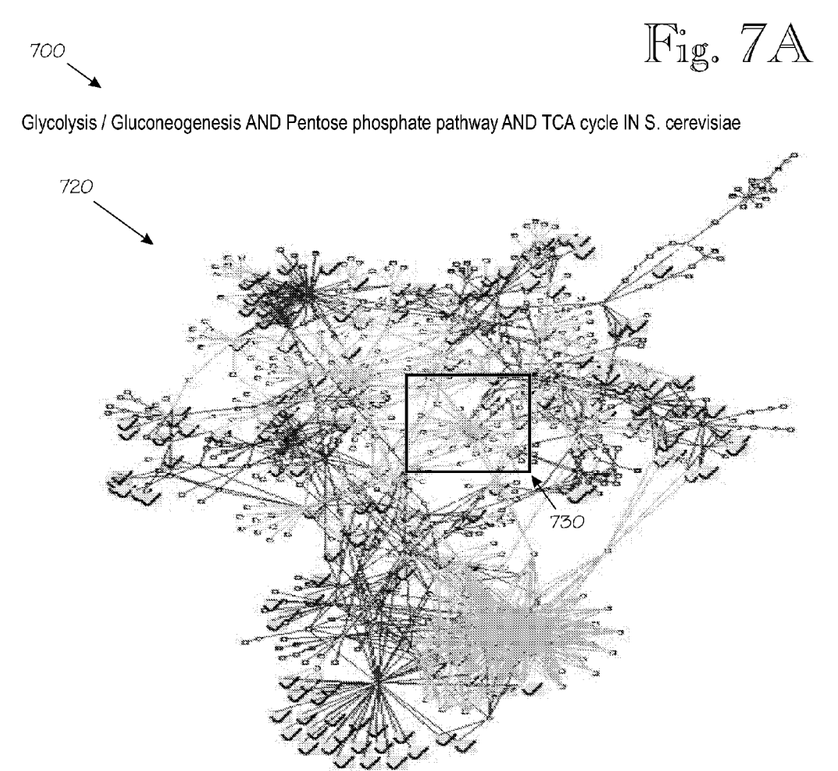
FIGS. 7A and 7B illustrate the results of query processing.
Figure 7B:
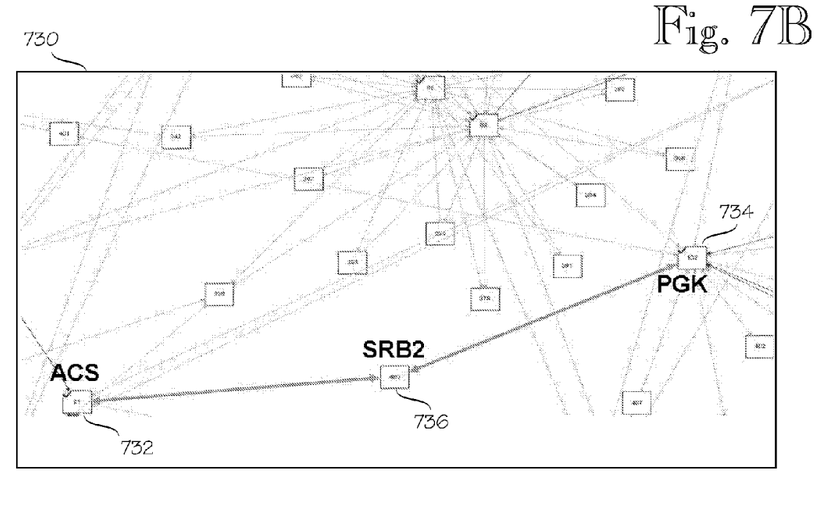

The invention is applicable to the study of metabolic pathways, enriched with information about known molecular interactions at the level of protein-protein interactions, regulatory and signalling networks. FIGS. 7A and 7B illustrate the results of query processing. In FIG. 7A, reference numeral 700 denotes an exemplary query, in which the slash character "/" is part of the pathway name (Glycolysis/Gluconeogenesis).

In this example, the query was set up to first search the KEGG database (shown as external databases 150 in FIG. 1) and retrieve the primary components of the pathways, ie, enzymes and compounds. In a second phase, the database traversals were used to search protein-protein interaction databases BIND and MINT for interactions of the enzymes with the nearest neighbour proteins, ie, interaction search depth was set to one. Reference numeral 720 denotes the resulting network which shows a surprisingly high level of connectivity across different stages of linear metabolic pathways via protein-protein interactions.

Reference numeral 730 denotes a region which is shown magnified in FIG. 7B. In the region 730, the focus is on two enzymes from the glycolysis pathway: Phosphoglycerate kinase (PGK; EC 2.7.2.3), denoted by reference numeral 732 and Acetate-CoA ligase (ACS; EC 6.2.1.1), denoted by reference numeral 734. ACS 734 catalyses formation of acetyl-CoA from acetate, which as a starting point in the TCA cycle, while PGK 732 catalyses acetylation of 3-phospho-D-glycerate, which is part of the second phase of glycolysis. Both enzymes appear to aggregate with SRB2, denoted by reference numeral 736.

Notably, SRB2 is involved in transcriptional initiation. This could mean that PGK and ACS, enzymes at two different stages of glycolysis, are coregulated.

Figure 8:
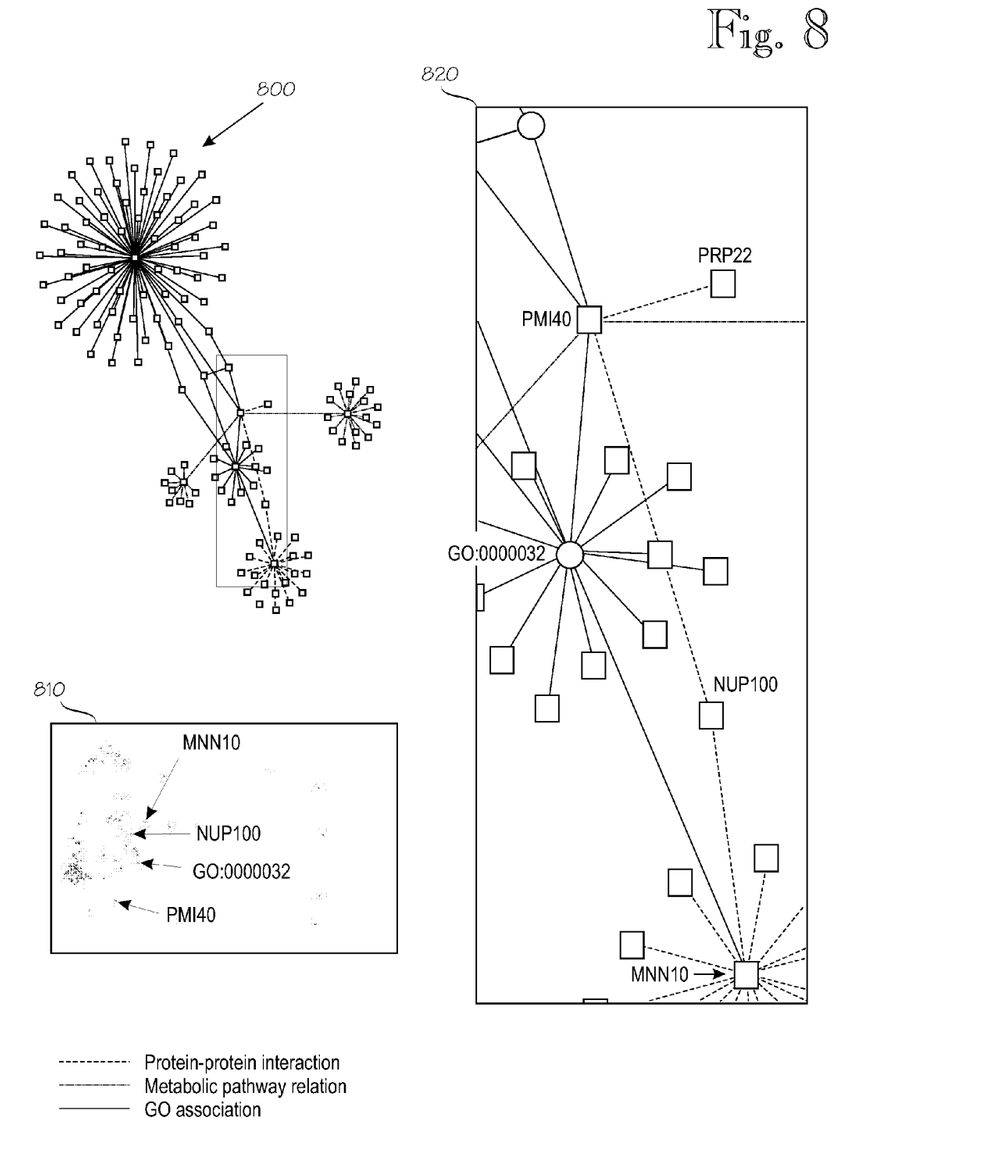
FIG. 8 illustrates a search to a protein's neighbourhood.

FIG. 8 illustrates another example which involves a search to a protein's neighbourhood. In this example, the system according to an embodiment of the invention was set up to search for the network neighbourhood of Mannose-6-phosphate isomerase (PMI40) in *Saccharomyces cerevisiae* (yeast). In FIG. 8, protein-protein interactions are shown by dashed lines, Metabolic pathway relationships are shown by dash-dot lines and GO associations by solid lines. Both PMI40 and MNN10 are involved in cell wall mannoprotein synthesis (GO:0000032). NUP100 protein, which is part of the nuclear pore complex, appears to interact with the PMI40 and MNN10 genes.

Assignment of protein function is a non-trivial task due to the fact that the same proteins may be involved in different biological processes, depending on the state of the biological system and protein localization. Therefore, protein function is dependent on context. The "protein neighbourhood", ie, the entities of the network close to the protein, may provide an insight about the protein function and its way of action. The entities can be either molecules, genes, or more complex concepts, and the proximity is measured by applying the distance measure. This example involved a search of the neighbourhood of Mannose-6-phosphate isomerase for *S. cerevisiae* (PMI40; UniProt Id: P29952), which catalyses the conversion between fructose 6-phosphate and mannose 6-phosphate and thus connects glycolysis with the cell wall synthesis in *S. cerevisiae*. The search involved concurrent retrieval of relationships for the following databases: UniProt, KEGG, BIND, MINT, and GO Biological Process (shown as external databases 150 in FIG. 1). For any nearest-neighbour protein-protein association, such as protein-protein interaction or sharing the same GO class at the lowest level, the distance was set to 1. In case of metabolic pathways, the weight of each connection was set to 0.5 in the direction of possible reaction. Search depth was set to two nearest proteins if the first of the connections was a protein-protein interaction, and to the nearest protein otherwise. This included cases where the nearest protein was connected to the search protein via the compound in metabolic pathways or the lowest level GO term. Reference numeral 800 denotes the resulting network visualization, while reference numeral 810 denotes the mapping of the nearest protein neighbours of PMI40. Sammon's mapping was used in this example.

Reference numeral 820 denotes a zoomed-in window of the network visualization 800. The zoomed-in window 820 shows a region of potential interest, which includes protein-protein interactions between the PMI40 and NUP100 (UniProt Id: Q02629), which is a subunit of the nuclear pore complex, as well as between alpha-1,6-mannosyltransferase (MNN10; UniProt Id: P50108) and NUP100. According to Gene Ontology (GO:0000032), both PMI40 and MNN10 are also involved in cell wall mannoprotein synthesis. While PMI40 is kind of a gate between cell wall synthesis and glycolysis, ie, cell decision point between growth or energy production, MNN10 is a part of the protein complex in mannoprotein synthesis toward the end of the cell wall biosynthesis pathways. Examination of interaction entries (BIND Id's 137955 and 137823, respectively) suggests that NUP100 protein, which is a part of nuclear pore complex, binds to the PMI40 and MNN10 open reading frames. This provides support for the "gene-gating" hypothesis, which suggests that the interaction of the nuclear pore complex with different genes might serve as a level of gene regulation. One testable hypothesis, which is the result of this experiment, is that PMI40 and MNN10 are indeed coregulated in relation to cell decision-making between energy production vs. growth.

References:
1. Cox, T. F., Cox, M. A. A. (2001) *Multidimensional scaling*, Chapman & Hall/CRC, Boca Raton.
2. Kohonen, T. (2001) *Self organizing maps*, Springer Verlag.
3. Sammon Jr., J. W. (1969) A nonlinear mapping for data structure analysis. *IEEE Trans. Comp.*, C-18, 401-409.
4. Torgerson, W. S. (1952) Multidimensional scaling: I. Theory and method. *Psychometrika*, 17, 401-419.

The invention claimed is:

1. A method for controlling operation of a computerized visualization system, in order to visualize biological information, the method comprising the following steps performed by the computerized visualization system:
　generating a user interface and receiving a user query relating to biological information via the generated user interface;
　maintaining connections to a plurality of databases which store at least partially non-overlapping biological information;
　determining which database of the plurality of databases contains the biological information relating to the received query;
　sending a database query to the determined database and receiving a result of the database query, the result comprising entities that are biological and relations between the entities;
　creating a network based on the result of the database query, wherein the network-creating step comprises mapping the entities to network nodes and the relations to network connections;
　determining a distance matrix for indicating a distance for several pairs of network nodes, each distance being calculated across several dimensions;
　applying a dimensionality reduction function to map the distance matrix to a lower number of dimensions;
　searching for neighbors of a selected network node based on the distance matrix in order to elucidate a biological role of the selected network node;
　adjusting the dimensionality reduction function based on one or more research contexts of the biological information, in order to bias the search toward a relevant focus; and
　re-creating and visualizing the network based on the adjusted dimensionality reduction function.

2. A method according to claim 1, further comprising mapping each of the one or more research contexts to a network node.

3. A method according to claim 2, further comprising combining results of multiple database queries to different databases into a single network.

4. A method according to claim 2, wherein the mapping step comprises mapping from several dimensions to two dimensions.

5. A method according to claim 1, further comprising combining results of multiple database queries to different databases into a single network.

6. A method according to claim 5, wherein the mapping step comprises mapping from several dimensions to two dimensions.

7. A method according to claim 1, wherein the mapping step comprises mapping from several dimensions to two dimensions.

8. A method according to claim 1, wherein the distance function is based on network topology.

9. A method according to claim 8, wherein the distance function is based on relationships from experimental data.

10. A method according to claim 1, wherein the distance function is based on relationships from experimental data.

11. A method according to claim 10, wherein the relationships from experimental data comprise a correlation measure.

12. A tangible, non-transient computer program product, executable in a computer, wherein execution of the computer program product causes the computer to carry out the steps of claim 1.

13. A computer system, comprising the computer program product according to claim 12.

* * * * *

UNITED STATES PATENT AND TRADEMARK OFFICE
CERTIFICATE OF CORRECTION

PATENT NO.        : 8,572,064 B2                                                                 Page 1 of 1
APPLICATION NO. : 11/912900
DATED             : October 29, 2013
INVENTOR(S)       : Oresic et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1493 days.

Signed and Sealed this
Twenty-second Day of September, 2015

Michelle K. Lee
*Director of the United States Patent and Trademark Office*